United States Patent [19]

Heiker et al.

[11] Patent Number: 4,537,881
[45] Date of Patent: Aug. 27, 1985

[54] 5-NITRO 1,4-DIHYDROPYRIDINES HAVING A POSITIVE INOTROPIC EFFECT

[75] Inventors: Fred R. Heiker, Wuppertal; Jürgen Stoltefuss, Haan; Gerhard Franckowiak, Wuppertal; Matthias Schramm, Cologne; Günter Thomas; Rainer Gross, both of Wuppertal, all of Fed. Rep. of Germany

[73] Assignee: Bayer Aktiengesellschaft, Leverkusen, Fed. Rep. of Germany

[21] Appl. No.: 627,596

[22] Filed: Jul. 3, 1984

[30] Foreign Application Priority Data

Jul. 22, 1983 [DE] Fed. Rep. of Germany ....... 3326384

[51] Int. Cl.³ ................ A61K 31/41; A61K 31/395; C07D 405/12
[52] U.S. Cl. .................................... 514/25; 536/17.3; 536/18.1; 546/271; 546/268; 546/310
[58] Field of Search ...................... 546/271, 268, 310; 536/17.3, 18.1; 424/266, 180

[56] References Cited

PUBLICATIONS

Bossert, et al., "4-Aryldihydropyridines", Angew. Chem. Int. Ed. Engl. 20, (1981), pp. 762-769.

Primary Examiner—Henry R. Jiles
Assistant Examiner—Dale A. Bjorkman
Attorney, Agent, or Firm—Sprung Horn Kramer & Woods

[57] ABSTRACT

Novel 1,4-dihydropyridines of the fomula

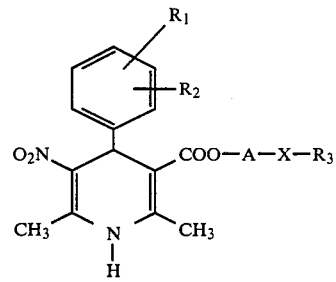

in which $R_1$ and $R_2$ each independently is hydrogen, $C_1$-$C_4$-alkyl, $C_1$-$C_{12}$-alkoxy, $C_1$-$C_4$-halogenoalkoxy, halogen, nitro, $C_1$-$C_4$-halogenoalkyl, $C_1$-$C_4$-halogenoalkylmercapto,

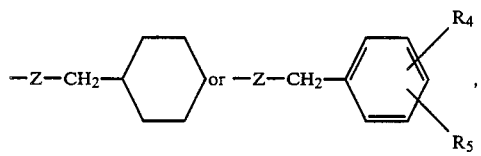

in which
Z is oxygen or sulphur, and
$R_4$ and $R_5$ each independently is hydrogen, $C_1$-$C_4$-alkyl, $C_1$-$C_6$-alkoxy, halogen, $C_1$-$C_4$-halogenoalkyl, $C_1$-$C_4$-halogenoalkoxy or nitro, or
$R_1$ and $R_2$, together with 2 C atoms of the phenyl ring, form the ring

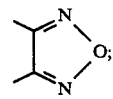

X is oxygen, sulphur or the radical $NR_6$,
$R_6$ is a $C_1$-$C_6$-alkyl group,
A is a $C_2$-$C_{10}$-alkylene group, it being necessary that at least two C atoms are located in the alkylene chain which connects the carbonyloxy group to X, and
$R_3$ is a monosaccharide or disaccharide moiety or a protected monosaccharide or disaccharide moiety,
or pharmaceutically acceptable addition salts thereof, which exhibit positive inotropic activity and are useful in treating circulatory disorders.

9 Claims, No Drawings

5-NITRO 1,4-DIHYDROPYRIDINES HAVING A POSITIVE INOTROPIC EFFECT

The present invention relates to new 1,4-dihydropyridines, processes for their preparation and their use in medicaments, in particular in medicaments acting on the circulatory system and having a positive inotropic effect.

It has already been disclosed that 1,4-dihydropyridines have vasodilator properties and can be used as coronary agents and antihypertensives (compare British Pat. No. 1,173,062; British Pat. No. 1,358,951; DE-OS (German Published Specification) No. 2,629,892 and DE-OS (German Published Specification) No. 2,752,820). It has also been disclosed that 1,4-dihydropyridines, being calcium antagonists, bring about depression of the contractility of smooth muscle and myocardium and can be employed for the treatment of coronary and vascular diseases (compare A. Fleckenstein, Ann. Rev. Pharmacol. Toxicol. 17, 149–166 (1977)).

Knowing these properties of the dihydropyridines, it could not have been foreseen that the compounds which are mentioned below from this class of substances do not have an action which depresses contractions, but have a positive inotropic effect on the myocardium which increases contractility.

The present invention relates to new 1,4-dihydropyridine derivatives of the general formula (I)

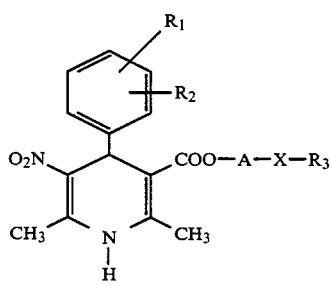

in which: $R_1$ and $R_2$, which can be identical or different, represent hydrogen, $C_1$–$C_4$-alkyl, $C_1$ to $C_{12}$-alkoxy, $C_1$–$C_4$-halogenoalkoxy, halogen, nitro, $C_1$–$C_4$-halogenoalkyl, $C_1$–$C_4$-halogenoalkylmercapto or one of the groups

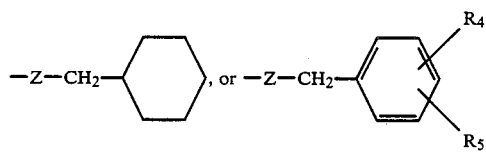

in which

Z denotes oxygen or sulphur, and $R_4$ and $R_5$, which can be identical or different, denote hydrogen, $C_1$–$C_4$-alkyl, $C_1$–$C_6$-alkoxy, halogen, $C_1$–$C_4$-halogenoalkyl, $C_1$–$C_4$-halogenoalkoxy or nitro, or $R_1$ and $R_2$, together with 2 C atoms of the phenyl ring, form the ring

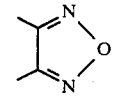

X represents oxygen, sulphur or the radical, $NR_6$, $R_6$ denoting a $C_1$–$C_6$-alkyl group, A represents a $C_2$–$C_{10}$-alkylene group, it being necessary that at least two C atoms are located in the alkylene chain which connects the carboxyl group to X, and $R_3$ represents a monosaccharide or disaccharide moiety which is, where appropriate, provided with the protective groups customary in carbohydrate chemistry, and their pharmaceutically acceptable acid addition salts.

Halogens which may be mentioned as preferred are fluorine, chlorine or bromine, in particular fluorine or chlorine.

Examples of salts which may be mentioned are: hydrochlorides, bisulphates, acetates, maleates, The moiety $R_3$ preferably represents the following: hexoses, such as allose, fructose, sorbose, altrose, glucose, mannose, gulose, idose, galactose or talose; pentoses, such as ribose, arabinose, xylose and lyxose; glucosamine; and disaccharides, such as maltose, lactose, lactosamine, cellobiose and trehalose; all groups being in the pyranose or furanose form and provided, where appropriate, with the protective groups customary in carbohydrate chemistry.

The following may be particularly mentioned: hexoses, such as glucose, mannose and galactose; and pentoses, such as ribose, xylose and arabinose.

The customary protective groups which are preferably detailed are the following: acyl groups, such as acetyl or benzoyl; ethers which can be cleaved by acid, such as trityl or silyl; acetals and ketals, such as isopropylidene, cyclohexylidene, benzylidene and tetrahydro pyranoyl; and ethers which can be eliminated by hydrogenolysis, such as benzyl.

Preferred compounds of the formula (I) are those in which $R_1$ represents hydrogen, $R_2$ represents halogen, trifluoromethyl, nitro, hydrogen or one of the groups

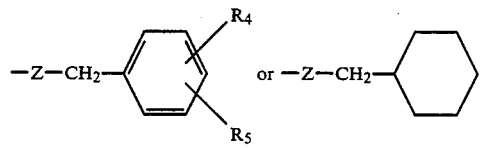

Z, $R_4$ and $R_5$ representing the meanings already indicated, $R_3$ represents a monosaccharide moiety which is, where appropriate, provided with protective groups, X denotes oxygen or sulphur and A represents a $C_2$–$C_6$-alkylene group.

The dihydropyridines of the general formula (I), according to the invention, can be prepared by (A) reacting aminocrotonic esters of the general formula (II)

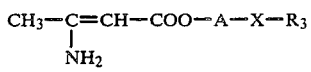

in which A, X and $R_3$ have the abovementioned meaning, with aldehydes of the general formula (III)

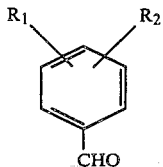

in which $R_1$ and $R_2$ have the abovementioned meaning, and nitroacetone $$CH_3-CO-CH_2-NO_2$$

or (B) reacting benzaldehydes of the formula (III) with acetoacetic esters of the formula (IV)

$$CH_3-CO-CH_2-COO-A-X-R_3 \quad (IV)$$

in which A, X and $R_3$ have the abovementioned meaning, or their Knoevenagel condensation products of the formula (V)

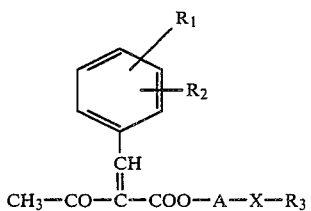

with an addition compound of nitroacetone and ammonia $$CH_3-CO-CH_2-NO_2-NH_3$$

or (C) by reacting aminocrotonic esters of the formula (II) with benzylidenenitroacetones of the formula (VI)

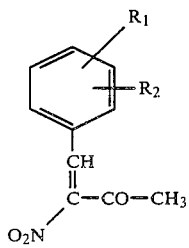

In general, in the methods of preparation the compounds of the formulae (II), (IV) and (V) employed are such that the carbohydrate substituent $R_3$ is in a protected form. Where desired and appropriate, elimination of the protective group is carried out by customary methods, for example by transesterification catalyzed by bases or acids for acyl protective groups, acid-catalyzed elimination of acetals, ketals, trityl or silyl groups, and hydrogenolysis of benzyl protective groups.

When, in process variant (A), for example, a β-aminocrotonic ester and benzaldehyde are reacted with nitroacetone, then the reaction can be represented by the equation below:

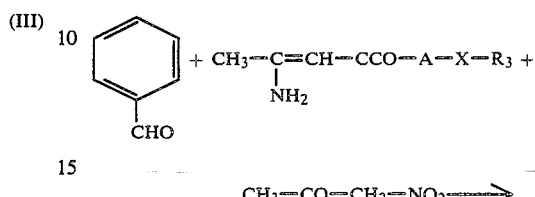

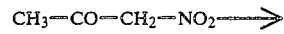

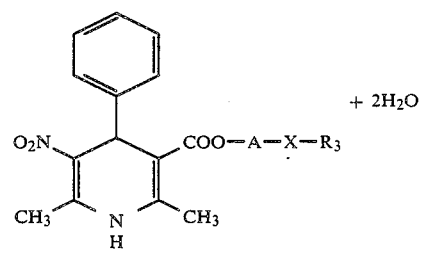

When, in process variant (B), for example, a 2-trifluorobenzylideneacetoacetic ester is reacted with nitroacetone/ammonia, then the reaction can be represented by the equation below,

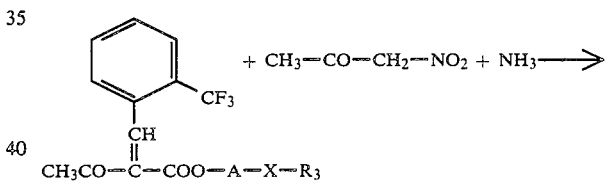

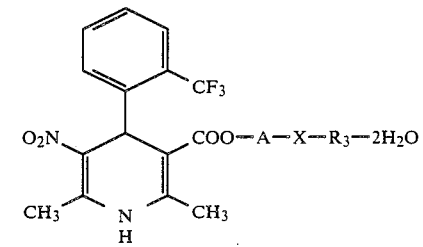

When, in process variant (C), for example, 2-benzyloxybenzylidenenitroacetone is reacted with an aminocrotonic ester, then the reaction can be represented by the equation below:

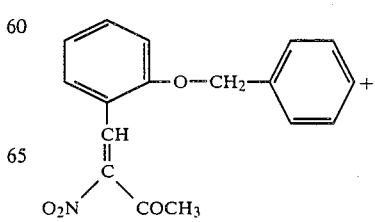

-continued

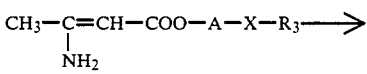

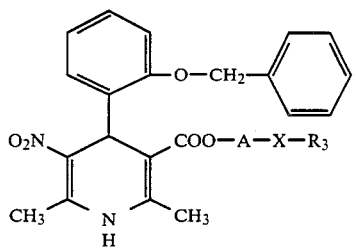

Suitable diluents for all the process variants (A), (B) and (C) are all inert organic solvents. These preferably include alcohols, such as ethanol, methanol or isopropanol, ethers, such as dioxane, diethyl ether, tetrahydrofuran, glycol monomethyl ether or glycol dimethyl ether, or glacial acetic acid, dimethylformamide, dimethyl sulphoxide, acetonitrile, pyridine and hexamethylphosphoric triamide.

The reaction temperatures can be varied within a fairly wide range. In general, the reactions are carried out between 20° and 150° C., but preferably at the boiling point of the particular solvent.

It is possible to carry out the reaction under atmospheric pressure or under elevated pressure. In general, it is carried out under atmospheric pressure.

The abovementioned preparation processes are merely given as illustrations, and the preparation of the compounds of the formula (I) is not restricted to these processes, but every modification of these processes can be used in the same manner for the preparation of the compounds according to the invention.

The ratio of amounts of the reactants to one another is arbitrary, equimolar amounts generally being employed. However, it has proved to be advantageous to employ up to a 5 molar excess of nitroacetone in process (A), and up to a 5 molar excess of the nitroacetone/ammonia adduct in process (B).

Depending on the choice of the starting substances, the compounds according to the invention can exist in stereoisomeric forms which are not related as image and mirror image (diastereomers). The present invention relates both to the diastereomers and to mixtures of diastereomers. The mixtures of diastereomers can be separated in a known manner (compare, for example, E. L. Eliel, Stereochemistry of Carbon Compounds, Mc Graw Hill, 1962).

The aminocrotonic esters of the formula (II) are not known, but they can be prepared by known methods from acetoacetic esters of the formula (IV) with ammonia, compare A. C. Cope, J. Am. Chem. Soc. 67, 1017 (1945).

Acetoacetic esters of the formula (IV) are known and can be prepared by methods known per se, by, for example, either (a) reacting furanosyl or pyranosyl halides with compounds of the formula HO—$(CH_2)_n$—XH, and reacting the resulting reaction product with diketone to give a compound of the formula (IV), or (b) preparing compounds of the formula (IV) with X=S, by first reacting ω-halogenoalcohols with diketene, and reacting the resulting ω-halogenoalkyl-acetoacetates with 1-thiopyranoses or 1-thiofuranoses, compare H. Paulsen, Angew. Chemie 94, 184–201 (1982); D. Borrmann, "Umsetzung von Diketen mit Alkoholen, Phenolen und Mercaptanen" (Reaction of Diketene with alcohols, phenols and mercaptans), in Houben-Weyl, Methoden der organischen Chemie (Methods of Organic Chemistry), Volume VII/4, 230 et seq. (1968); and Y. Oikawa, K. Sugano and O. Yonemitsu, J. Org. Chem. 43, 2087 (1978).

Aldehydes (III) used are known and can be prepared by methods known from the literature (compare T. D. Harris and G. P. Roth, J. Org. Chem. 44, 146 (1979); German Offenlegungsschrift (German Published Specification) No. 2,165,260; German Offenlegungsschrift (German Published Specification) No. 2,401,665; Mijano et al., Chem. Abstr. 59 (1963), 13 929 c; E. Alder and H.-D. Becker, Chem. Scand. 15, 849 (1961); and E. P. Papadopoulus, M. Mardin and Ch. Issidoridis, J. Org. Chem. 31, 615 (1966), J. Am. Chem. Soc. 78, 2543 (1956)).

The ylidene-β-carboxylic esters of the formula (V) which can be used according to the invention are not known, but they can be prepared by known methods [Organic Reactions XV, 204 et seq. (1967)].

The compounds of the formula (VI) which can be employed are known and are described in H. Dornoff and W. Sassenberg, Liebigs Ann. Chem. 602, 14 (1957).

The nitroacetone×$NH_3$ addition product can be prepared in analogy to H. Bohme and K.-H. Weisse Arch. Pharm., 310, 30 (1977).

Nitroacetone can be prepared by known methods (compare N. Levy and C. W. Scarfe, J. Chem. Soc. (London) (1946) 1103; and C. D. Hurd and M. E. Nilson, J. Org. Chem. 20, 927 (1955)).

The new active compounds can be converted in a known manner into the customary formulations, such as tablets, capsules, coated tablets, pills, granules, aerosols, syrups, emulsions, suspensions and solutions, using inert, non-toxic, pharmaceutically acceptable vehicles or salts. The therapeutically active compound should, in each case, be present in a concentration of about 0.5 to 90% by weight of the total mixture, that is to say in amounts which suffice to achieve the dosage range indicated.

The formulations are prepared, for example, by extending the active compounds with solvents and/or vehicles, optionally with the use of emulsifiers and/or dispersing agents and, for example, when using water as a diluent, organic solvents can optionally be used as auxiliary solvents.

Examples of auxiliaries which may be mentioned are: water, non-toxic organic solvents, such as paraffins (for example petroleum fractions), vegetable oils, (for example groundnut oil/sesame oil), alcohols (for example ethyl alcohol and glycerol), glycols (for example propylene glycol and polyethylene glycol), solid vehicles, such as, for example, natural rock powders (for example kaolins, aluminas, talc and chalk), synthetic rock powders (for example highly disperse silica and silicates), sugars (for example sucrose, lactose and glucose), emulsifiers (for example polyoxyethylene fatty acid esters), polyoxyethylene fatty alcohol ethers, alkylsulphonates and arylsulphonates), dispersing agents (for example lignin, sulphite waste liquors, methylcellulose, starch and polyvinylpyrrolidone) and lubricants (for example magnesium stearate, talc, stearic acid and sodium lauryl sulphate).

Administration is effected in the customary manner, preferably orally or parenterally, in particular perlingually or intravenously. In the case of oral administration, the tablets can, of course, also contain, in addition to the vehicles mentioned, additives such as sodium citrate, calcium carbonate and dicalcium phosphate, together with various additional substances, such as starch, preferably potato starch, gelatin and the like. Furthermore, lubricants such as magnesium stearate, sodium lauryl sulphate and talc, can also be used when making tablets. In the case of aqueous suspensions and or elixirs which are intended for oral use, the active compounds can be mixed with various flavor-improving agents or colorants in addition to the abovementioned auxiliaries.

In the case of parenteral administration, solutions of the active compound, employing suitable liquid vehicles, can be used.

In general, it has proved advantageous, in the case of intravenous administration, to administer amounts of about 0.001 to 1 mg/kg, preferably about 0.01 to 0.5 mg/kg, of body weight to achieve effective results, and in the case of oral administration, the dosage is about 0.01 to 20 mg/kg, preferably 0.1 to 10 mg/kg, of body weight.

Nevertheless, it can at times be necessary to deviate from the amounts mentioned, and in particular to do so as a function of the body weight of the experimental animal or of the nature of the administration method, but also because of the species of animal and its individual behavior toward the medicament, and the nature of the formulation of the medicament and the time or interval over which the administration takes place. Thus it can suffice in some cases to manage with less than the abovementioned minimum amount, whereas in other cases the upper limit mentioned must be exceeded. Where relatively large amounts are administered, it can be advisable to divide these into several individual administrations over the course of the day. The same dosage range is envisaged for administration in human medicine. In this connection, the above statements similarly apply.

The compounds according to the invention have a positive inotropic effect and thus exhibit a valuable spectrum of pharmacological effects which could not have been foreseen. They can be used as cardiotonics to improve the contractility of the heart. In addition, they can be employed as antihypotensives, to lower the blood sugar, to reduce the swelling of mucous membranes and to affect the salt and fluid balance.

The positive inotropic effect of the compounds of the formula (I), according to the invention, is determined in the following design of experiments; those compounds which, at a concentration of as low as $10^{-5}$ g/ml, exhibit a positive inotropic effect on the left atrium of the isolated guinea-pig heart are to be particularly preferred:

The left atria of guinea-pig hearts are isolated and suspended in a thermostatic organ bath which contains an isotonic mineral salt solution, which is adjusted to be appropriate for the ionic medium and the pH of body fluid, and suitable nutrients. A gas mixture comprising oxygen and carbon dioxide is passed through this organ bath, the content of carbon dioxide being adjusted so that the pH of the organ bath remains constant. The left atria are tensioned in the organ bath and the tension is recorded by a force sensor, a particular basal tone being set up. Then the left atria are continuously subjected to electrical stimulation at set intervals, and the contractions which take place are recorded. After addition of the active compound, the contractions are again recorded. A strengthening in the contractions by at least 25% is regarded as a significant positive inotropic effect.

Thus for example, the contractions of the left guinea-pig atrium electrically stimulated at 1 Hz are strengthened by 32% by $10^{-6}$ g/ml of the compound from Example 1, and by 47% by the compound from Example 2.

EXAMPLE 1

2-O-(2,3,4,6-tetra-O-acetyl-β-D-1-glucopyranosyl)ethyl 1,4-dihydro-2,6-dimethyl-3-nitro-4-(2-benzyloxyphenyl)pyridine-5-carboxylate

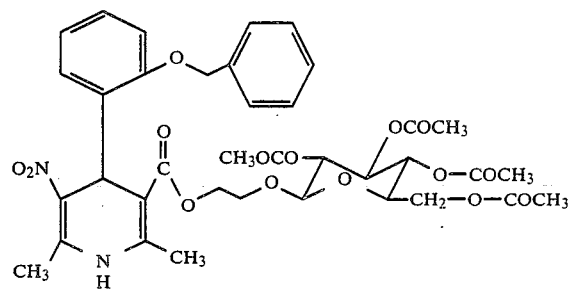

Process variant (A)

2.7 g (12.5 mmol) of 2-benzyloxybenzaldehyde are heated to reflux with 5.9 g (12.5 mmol) of 2-O-(2,3,4,6-tetra-O-acetyl-β-D-1-glucopyranosyl)ethyl aminocrotonate and 2.25 g (21.88 mmol) of nitroacetone in 50 ml in ethanol for 3½ hours and the mixture is then evaporated. The residue resulting from evaporation is then separated over a column of length 35 cm and diameter 5 cm (volume 690 cm³) with silica gel 60, 0.04–0.063 mm (Merck) as the stationary phase and with toluene/ethyl acetate in the volume ratio 6:1, and later 4:1. The almost pure fractions are combined and evaporated. 3.7 g (39.3% of theory) of a resinous yellow product, which crystallizes on trituration with ether, are obtained. It is filtered off with suction, washed with ether and dried. 2.5 g (26.5% of theory) of yellow crystals of melting point 103°–105° C. are obtained.

EXAMPLE 2

2-O-(β-D-1-Glucopyranosyl)ethyl 1,4-dihydro-2,6-dimethyl-3-nitro-4-(2-benzyloxy)-phenylpyridine-5-carboxylate

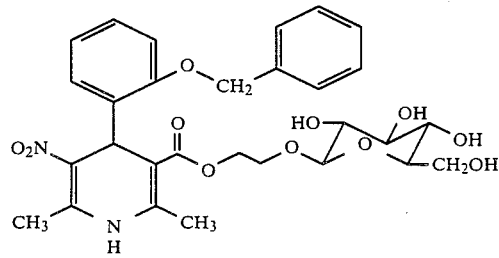

2.5 g (3.32 mmol) of the compound from Example 1 are dissolved in 25 ml of absolute methanol, and 1 ml of 1 molar sodium methylate solution is added with stirring, whereupon the color of the solution changes from yellow to red. After 15 minutes, the progress of deprotection is checked by thin layer chromatography. Since the reaction is as yet incomplete, a further 0.5 ml of 1 molar sodium methylate solution is added. The reaction is complete after 15 minutes. The mixture is neutralized by adding Amberlite IR 120 ion exchanger, then filtered and evaporated. The crystalline residue from evaporation is stirred with ether/methanol 3:1, filtered off with suction and washed with ice-cold methanol and ether. 1.7 g (92.14% of theory) of product is obtained in the form of yellow crystals of melting point 138°–140° C.

Rf value 0.37, TLC aluminum roll, silica gel 60 F 254 (Merck)

Mobile phase: chloroform/methanol in the volume ratio 5:1.

The following were obtained in analogy to Example 1:

Rf values: TLC aluminum roll silica gel 60 F 154 (Merck);

Mobile phase: toluene/ethanol in the volume ratio 10:1.

EXAMPLE 3

2-O-(2,3,4,6-tetra-O-acetyl-β-D-1 -glucopyranosyl-)ethyl 1,4-dihydro-2,6-dimethyl-3-nitro-4-[2-(4-methylbenzyloxy)phenyl]pyridine-5-carboxylate, isolated as a foam.

Rf values: 0.3.

EXAMPLE 4

2-S-(2,3,4-tri-O-acetyl-1-thio-β-L-1-arabinopyranosyl)ethyl 1,4-dihydro-2,6-dimethyl-3-nitro-4-(2-benzyloxyphenyl)pyridine-5-carboxylate of melting point 116°–18° C.

EXAMPLE 5

3-S-(2,3,4,6-tetra-O-acetyl-1-thio-β-D-1-glucopyranosyl)-n-propyl 1,4-dihydro-2,6-dimethyl-3-nitro-4-[2-(4-fluorobenzylmercapto)phenyl]pyridine-5-carboxylate.

Rf value: 0.295

EXAMPLE 6

3-O-(2,3,4,6-tetra-O-acetyl-β-D-1-glycopyranosyl)-n-propyl 1,4-dihydro-2,6-dimethyl-3-nitro-4-(2-benzyloxyphenyl)pyridine-5-carboxylate.

Rf value: 0.305.

EXAMPLE 7

3-S-(2,3,4,6-tetra-O-acetyl-1-thio-β-D-1-glucopyranosyl)-n-propyl 1,4-dihydro-2,6-dimethyl-3-nitro-4-(2-benzyloxyphenyl)pyridine-5-carboxylate.

Rf value: 0.33.

EXAMPLE 8

2-S-(2,3,4,6-tetra-O-acetyl-1-thio-β-D-1-glucopyranosyl)ethyl 1,4-dihydro-2,6-dimethyl-3-nitro-4-(2-benzyloxyphenyl)pyridine-5-carboxylate.

Rf value: 0.315.

EXAMPLE 9

2-O-(2,3,4,6-tetra-O-acetyl-β-D-1-glucopyranosyl-)ethyl 1,4-dihydro-2,6-dimethyl-3-nitro-4-[2-(4-fluorobenzyloxy)phenyl]pyridine-5-carboxylate.

Rf value: 0.275.

EXAMPLE 10

2-O-(2,3,4,6-tetra-O-acetyl-β-D-1-glucopyranosyl-)ethyl 1,4-dihydro-2,6-dimethyl-3-nitro-4-(2-trifluoromethylphenyl)pyridine-5-carboxylate.

Rf value: 0.21

EXAMPLE 11

2-O-(2,3,4,6-tetra-O-acetyl-β-D-1-glycopyranosyl-)ethyl 1,4-dihydro-2,6-dimethyl-3-nitro-4-phenylpyridine-5-carboxylate.

Rf value: 0.26

The following were prepared in analogy to Example 2:

(Rf values: TLC aluminum roll silica gel 60, F 254 (Merck),

Mobile phase:chloroform/methanol in the volume ratio 5:1.

EXAMPLE 12

2-O-(β-D-1-glucopyranosyl)ethyl 1,4-dihydro-2,6-dimethyl-3-nitro-4[2-(4-methylbenzyloxy)phenyl]pyridine-5-carboxylate of melting point 163° C.

EXAMPLE 13

2-S-(1-thio-β-D-1-arabinopyranosyl)ethyl 1,4-dihydro-2,6-dimethyl-3-nitro-4(2-benzyloxyphenyl)pyridine-5-carboxylate of melting point 121° C.

EXAMPLE 14

2-S-(1-thio-β-D-1-glucopyranosyl)ethyl 1,4-dihydro-2,6-dimethyl-3-nitro-4-(2-benzyloxyphenyl)pyridine-5-carboxylate of melting point 60°–70° C. with decomposition.

EXAMPLE 15

3-S-(1-thio-β-D-1-glucopyranosyl)-n-propyl 1,4-dihydro-2,6-dimethyl-3-nitro-4-(2-benzyloxyphenyl)-pyridine-5-carboxylate of melting point 120°–125° C.

EXAMPLE 16

3-O-(β-D-1-glycopyranosyl)-n-propyl 1,4-dihydro-2,6-dimethyl-3-nitro-4-(2-benzyloxyphenyl)pyridine-5-carboxylate.

Rf value: 0.52

EXAMPLE 17

3-S-(1-thio-β-D-1-glucopyranosyl)-n-propyl 1,4-dihydro-2,6-dimethyl-3-nitro-4-[2-(4-fluorobenzyloxy)phenyl]pyridine-5-carboxylate.

Rf value: 0.54

EXAMPLE 18

2-O-(β-D-1-glucopyranosyl)ethyl 1,4-dihydro-2,6-dimethyl-3-nitro-4-[2-(4-fluorobenzyloxy)phenyl]pyridine-5-carboxylate.

Rf value: 0.35

EXAMPLE 19

2-O-(β-D-1-glucopyranosyl)ethyl 1,4-dihydro-2,6-dimethyl-3-nitro-4-phenylpyridine-5-carboxylate.

Rf value: 0.25

EXAMPLE 20

Process variant (C)

1.06 g (5 mmol) of 2-benzyloxybenzaldehyde are stirred with 2.4 g (5 mmol) of 2-O-(2,3,4,6-tetracetyl-β-

D-glucopyranosyl)ethyl acetoacetate and 0.9 g (7.5 mmol) of nitroacetone/ammonia adduct in 10 ml of ethanol at 60° C. for 1 hour. The mixture is then heated to reflux for 3 hours. It is then evaporated. The residue from evaporation is separated on a column of length 17 cm and diameter 4.5 cm (volume=270 cm³) with silica gel 60, 0.04–0.063 mm (Merck) as the stationary phase and with toluene and ethyl acetate in the volume ratio 6:1, later 5:1, 4:1 and 3:1. The product is obtained at a volume ratio of 1:1. The fractions containing the product are evaporated. 220 mg (5.8% of theory) of a compound which is identical with the substance from preparation Example 1 are obtained.

EXAMPLE 21

Process variant (B)

1.75 g (6 mmol) of a compound of the formula

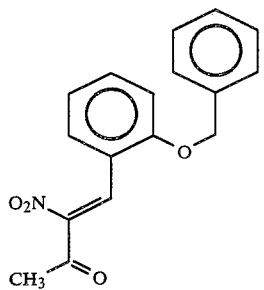

are stirred under reflux overnight with 2.6 g (6 mmol) 3-O-(2,3,4-tri-O-acetyl-α-L-1-arabinopyranosyl)propyl aminocrotonate

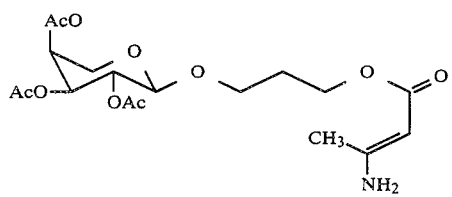

in 20 ml of ethanol. The mixture is evaporated and separated over about 50 g of 230–400 mesh silica gel in toluene: acetone 20:1; 10:1.

1.3 g (32%) are obtained.

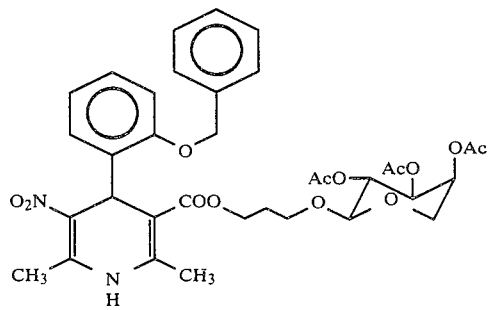

RF value: 0.28 (toluene/acetone 4:1), 0.38 (toluene/ethanol 6:1).

EXAMPLE 22

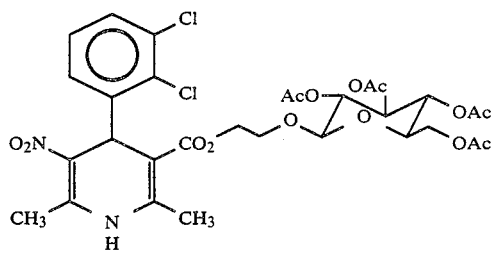

prepared by process variant (A)

Rf value: 0.2 (toluene/acetone 4:1), 0.34 (toluene/ethanol 6:1).

EXAMPLE 23

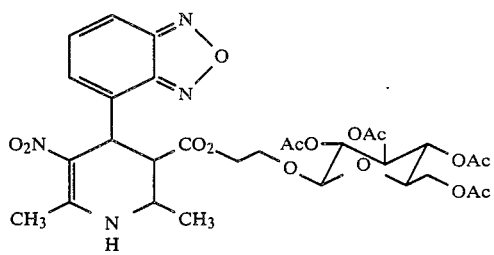

prepared by process variant (A)

Rf value: 0.24 (toluene/acetone 4:1), 0.34 (toluene/ethanol 6:1).

Preparation of the starting materials of the formula II or IV

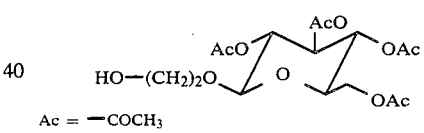

Ac = —COCH₃

48 g of acetobromoglucose (117 mmol) are vigorously stirred in 500 ml of toluene, 320 g of glycol and 57.6 g of silver carbonate (208 mmol) at 20° C. for 15 hours and then the mixture is filtered with suction. The toluene phase is separated off and the glycol phase is extracted 4× with toluene. The combined and dried phases are evaporated, and the substances crystallized from isopropanol.

27 g of crude product (59% of theory) are obtained. Melting point: 97°–99° C.

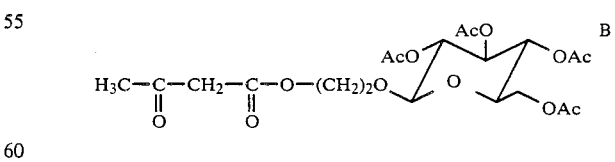

27 g of A are dissolved in 20 ml of toluene. After adding 1 ml of triethylamine, 8.2 g of diketene are added dropwise at 80° C. The mixture is stirred at 100° C. for 1 hour and then poured, with stirring, into a mixture of 200 ml of 5% strength NaHCO₃ solution and 100 ml of toluene. The toluene phase is separated off, the aqueous phase is again extracted by shaking with toluene, and the organic phases are dried and evaporated. After crystallization from isopropanol, 27.4 g of pure product (83.6% of theory) are obtained.

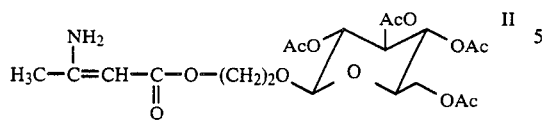

27.4 g of B are dissolved in 150 ml of toluene and, with the addition of 1 g of p-toluenesulphonic acid, the solution is stirred at 110° C. in a stream of ammonia under a water separator for 10 hours. After cooling, filtering with suction and evaporating, the product crystallizes from isopropanol. 19.7 g of crude substance (72%) of melting point 92°–94° C. are obtained.

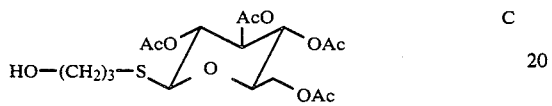

16.7 g of 3-bromo-1-propanol in 60 ml of acetone are added to 36.3 g (100 mmol) of 1-S-2,3,4,6-tetra-D-acetyl-β-O-glucopyranose in 60 ml of acetone and 8.3 g of $K_2CO_3$ in 100 ml of $H_2O$. After stirring at 20° C. for 2 hours, 300 ml of $CHCl_3$ and 100 ml of water are added to the mixture. The organic phase is separated off, and the aqueous phase is extracted 1× with $CHCl_3$. The combined organic phases are now extracted 1× with 2N HCl and 1× with saturated sodium chloride solution, dried and evaporated. 42 g (100%) of C are obtained, and this is pure enough for further reaction.

It will be appreciated that the instant specification and examples are set forth by way of illustration and not limitation, and that various modifications and changes may be made without departing from the spirit and scope of the present invention.

What is claimed is:

1. A 1,4-dihydropyridine of the formula

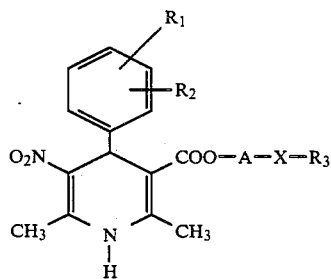

in which $R_1$ and $R_2$ each independently is hydrogen, $C_1$–$C_4$-alkyl, $C_1$–$C_{12}$-alkoxy, $C_1$–$C_4$-halogenoalkoxy, halogen, nitro, $C_1$–$C_4$-halogenoalkyl, $C_1$–$C_4$-halogenoalkylmercapto,

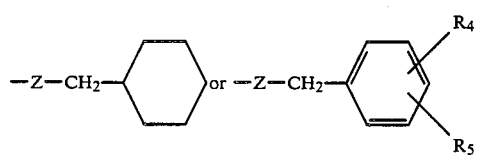

in which

Z is oxygen or sulphur, and $R_4$ and $R_5$ each independently is hydrogen, $C_1$–$C_4$-alkyl, $C_1$–$C_6$-alkoxy, halogen, $C_1$–$C_4$-halogenoalkyl, $C_1$–$C_4$-halogenoalkoxy or nitro, or $R_1$ and $R_2$, together with 2 C atoms of the phenyl ring, form the ring

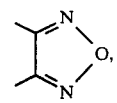

X is oxygen, sulphur or the radical $NR_6$, $R_6$ is a $C_1$–$C_6$-alkyl group,

A is a $C_2$–$C_{10}$-alkylene group, it being necessary that at least two C atoms are located in the alkylene chain which connects the carbonyloxy group to X, and $R_3$ is a monosaccharide or disaccharide moiety or a protected monosaccharide or disaccharide moiety, or a pharmaceutically acceptable addition salt thereof.

2. A compound or salt according to claim 1, in which $R_1$ is hydrogen, $R_2$ is halogen, trifluoromethyl, nitro, hydrogen,

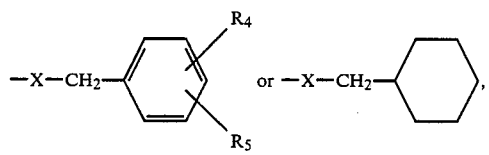

X is oxygen or sulphur,

A is a $C_2$–$C_6$-alkylene group, and $R_3$ is a monosaccharide moiety or a protected monosaccharide moiety.

3. A compound according to claim 1, wherein such compound is 2-O-(2,3,4,6-tetra-O-acetyl-β-D-1-glucopyranosyl)ethyl 1,4-dihydro-2,6-dimethyl-3-nitro-4-(2-benzyloxyphenyl)pyridine-5-carboxylate of the formula

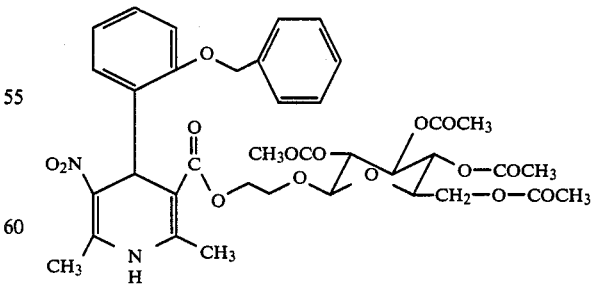

4. A compound according to claim 1, wherein such compound is 2-O-(β-D-1-glucopyranosyl)ethyl 1,4-dihydro-2,6-dimethyl-3-nitro-4-(2-benzyloxy)phenyl-pyridine-5-carboxylate of the formula 5. A compound according to claim 1, wherein such compound is 2-O-(β-D-1-glucopyranosyl)ethyl 1,4-dihydro-2,6-dimethyl-3-nitro-4-[2-(4-fluorobenzyloxy)-phenyl]pyridine-5-carboxylate of the formula

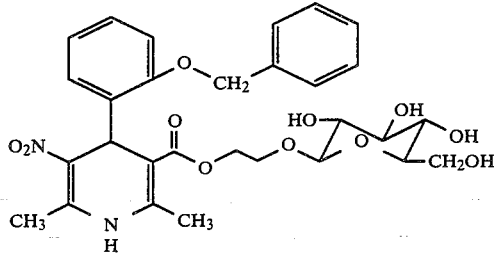

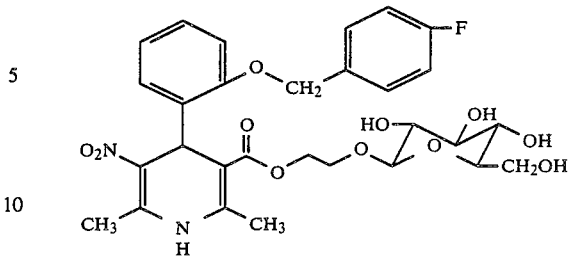

6. A composition for improving the myocardial contractility comprising an amount of a compound or salt according to claim 1 effective therefor plus a diluent.

7. A unit dose of a composition according to claim 6 in the form of a pill, capsule or ampule.

8. A method of improving the myocardial contractility of a patient comprising administering to such patient an amount effective therefor of a compound or salt according to claim 1.

9. The method according to claim 8, wherein such compound is

2-O-(2,3,4,6-tetra-O-acetyl-β-D-1-glucopyranosyl)ethyl 1,4-dihydro-2,6-dimethyl-3-nitro-4-(2-benzyloxyphenyl)pyridine-5-carboxylate, 2-O-(β-D-1-glucopyranosyl)ethyl 1,4-dihydro-2,6-dimethyl-3-nitro-4-(2-benzyloxy)phenylpyridine-5-carboxylate, or 2-O-(β-D-1-glucopyranoxyl)ethyl 1,4-dihydro-2,6-dimethyl-3-nitro-4-[2(4-fluorobenzyloxy)phenyl]-pyridine-5-carboxylate, or a pharmaceutically acceptable addition salt thereof.

* * * * *